(12) United States Patent
Coopersmith

(10) Patent No.: US 8,033,828 B2
(45) Date of Patent: Oct. 11, 2011

(54) CUSTOM IMPRESSION COPING AND METHODS OF MANUFACTURE AND USE THEREOF

(75) Inventor: Allan Coopersmith, Montreal (CA)

(73) Assignee: Allan Coopersmith, Montreal (CA)

( * ) Notice: Subject to any disclaimer, the term of this patent is extended or adjusted under 35 U.S.C. 154(b) by 432 days.

(21) Appl. No.: 12/091,884

(22) PCT Filed: Oct. 30, 2006

(86) PCT No.: PCT/CA2006/001821
§ 371 (c)(1),
(2), (4) Date: Apr. 28, 2008

(87) PCT Pub. No.: WO2007/048257
PCT Pub. Date: May 3, 2007

(65) Prior Publication Data
US 2009/0274999 A1    Nov. 5, 2009

Related U.S. Application Data

(60) Provisional application No. 60/730,883, filed on Oct. 28, 2005.

(51) Int. Cl.
*A61C 9/00* (2006.01)
(52) U.S. Cl. ........... 433/214; 433/215; 433/34; 433/136

(58) Field of Classification Search ................ 433/136, 433/214, 218, 223, 215, 40, 141, 138–139, 433/34, 226
See application file for complete search history.

(56) References Cited

U.S. PATENT DOCUMENTS

| | | | | |
|---|---|---|---|---|
| 5,676,543 | A | * | 10/1997 | Dragan ..................... 433/136 |
| 6,116,905 | A | | 9/2000 | Hoos |
| 7,153,134 | B2 | | 12/2006 | Coopersmith |

OTHER PUBLICATIONS

International Search Report of the International Application No. PCT/CA2006/001821.

* cited by examiner

*Primary Examiner* — Cris L Rodriguez
*Assistant Examiner* — Edward Moran
(74) *Attorney, Agent, or Firm* — Osler, Hoskin & Harcourt LLP

(57) ABSTRACT

A device for retracting gingival tissue away from a tooth or plurality of teeth prepared to receive a dental prosthesis comprising a retraction/impression material associated with a custom impression coping to be packed into a sulcus associated with the prepared tooth, and coincidentally obtaining an impression of said tooth or teeth. The device is preferably compressible, deformably rigid, extensile and non-elastic and will not stick to the gingiva or tooth structure thereby allowing for atraumatic removal. A method of use is also disclosed.

28 Claims, 12 Drawing Sheets

CUSTOM IMPRESSION COPING AND METHODS OF MANUFACTURE AND USE THEREOF

CROSS-REFERENCE TO RELATED APPLICATIONS

The present application is a 371 national stage of International Application No. PCT/CA06/001821, filed Oct. 30, 2006, which claims the benefit of priority to U.S. Provisional Patent Application No. 60/730,883, filed Oct. 28, 2005. It is related to, but does not claim the benefit of priority to, the following applications: Unites States Patent Application Publication No. 2005-0118552-A1, entitled "Gingival Retraction Device and Method", published Jun. 2, 2005; U.S. Pat. No. 7,033,173, entitled "Gingival Retraction Device and Method", published Apr. 25, 2006; and International Patent Application Publication No. WO/2002/102269, entitled "Gingival Retraction Device and Method", published Dec. 27, 2002. The contents of all of the aforementioned patents and patent applications are incorporated herein by reference.

FIELD OF THE INVENTION

The present invention relates to devices and methods employed by dental practitioners during dental procedures, and particularly in the preparation teeth for receiving dental restorations such as a crowns, veneers, inlays, onlays or implant supported prostheses.

BACKGROUND OF THE INVENTION

There many conventional dental procedures that require the taking of an impression of a tooth, or even more commonly, a tooth abutment. When taking an impression, as would evident, it is usually desirable to get the most accurate impression possible. One of the more difficult parts of the tooth or tooth abutment to accurately capture in the area around the base of tooth, and particularly in the area at the base of the tooth next to another tooth. One of the reasons for this difficulty is that a groove, called a sulcus, is formed in the gum tissue surrounding a tooth at the base thereof. This groove interferes with the taking of an impression.

Therefore, the process of retracting gum tissue forming the sulcus away from a moth abutment is customarily done prior to the taking of a dental impression. (Although some dentists claim that they can take impressions without the step of retraction, those impressions are often inaccurate and faulty, and depend on what is known in the art as a "total wash technique", using a low durometer material placed into a pre-set high durometer material, that creates a casting which is too tight and has an inaccurate fit.)

The purpose of retraction of the gingival tissue prior to the taking of an impression has been necessary in order to displace the gingival tissues away from the tooth and to create an open and dry sulcus. This will provide an impression that will be free of bubbles and other distortions (as the sulcus is open, dry and clear of bubbles, blood, saliva, and other debris), thereby producing an accurate impression.

Unfortunately, all current retraction systems and techniques have drawbacks. For example, most cord-type retraction systems are tedious, ineffective and traumatic to tissues. A known effort to improve the use of cords is the use of a kaolin type material that is mixed with an astringent salt and is simply placed about a prepared tooth to absorb the moisture to cause the gum tissue to shrink. Such a product is marketed by Sybron Dental Specialties under the brand name EXPA- SYL™. However, such kaolin type material is packaged in a cartridges that are inserted into a dispensing gun. The cartridges and the gun are expensive, and often break. The Kaolin is difficult to insert into the sulcus and requires rinsing and drying which often creates additional unwanted bleeding.

Another known retraction technique is to use a non-cord retraction and hemostasis such as that disclosed in Dragan, U.S. Pat. No. 5,676,543. Disclosed therein is a generally two-part process utilizing two different viscosities of a condensation silicone material to effect the cordless retraction and hemostasis of the gingival sulcus. This process is, however, time consuming and expensive and compresses the gingival in an inaccurate, ineffective and unpredictable manner. The gingival crest around the prepared abutment is compressed coincidentally with the compression into the sulcus thereby placing axial pressure on the sulcus. This causes the sulcus to partially collapse and renders a less accurate impression. Additionally, the same pressure is exerted on the abutments as is placed on the adjacent teeth which leads to inaccuracies and loss of operator control.

Most two step impression techniques are inaccurate in that the primary or preliminary impression is allowed to set over the teeth or gingiva to be restored, and then said impression is filled with a wash or impression material of a lesser durometer and reseated. Undercuts in the teeth and surrounding structures prevent the re-seating of the secondary impression leading to distortion and inaccuracies. Jahn, U.S. Pat. No. 3,882, 601 and Pumphrey, U.S. Pat. App. Pub. No. 2006-0172253 try to address the problem of distortion due to inaccurate repositioning of a secondary impression by creating an interstice or spacer material between the primary and secondary impression that is removed prior to taking the secondary impression, thereby reducing the undercuts and resultant distortion. Both of these inventions, however, require additional steps, are expensive, non-precise, inaccurate, and do not provide for simultaneous retraction as well as impression of the teeth and supporting structures. The result is frequent entrapment of bubbles and defective margins. When no spacer is utilized, two step impression techniques create inaccuracies and excessively tight fitting castings in that the softer or lower durometer wash impression material is overly compressed. If any part of the secondary impression is faulty or fails to adequately capture a tooth margin or other aspect of the structure to be restored, the entire impression technique must be completely repeated from the beginning because of the undercuts and repositioning inaccuracies as mentioned above.

Yet another retraction method is the use of a pressure cap. A pressure cap is a cap made of a spongy material that is fitted around the tooth and causes retraction of the gingival tissue through the application of pressure. The difficulty with retraction caps is that the shape of the cap is even and constant while that of the sulcus (both depth and width) is not. Therefore this method is imprecise and does not ensure accurate nor sufficient retraction. For these reasons, it is presently only used to ensure haemostatis after a procedure of gingival eviction.

Still additional retraction method is termed gingival eviction. In this method the gingival tissue is retracted by electric bistoury, laser, or by a diamond charged drill ("diamond curettage"). These procedures, however, are not without their drawbacks as well. Electric bistoury and laser generally mutilate the gingival tissue and are therefore quite painful and require local anaesthesia. Similarly diamond curettage is also quite painful and causes prolific bleeding. Each of these procedures is traumatic and creates gingival shrinkage and recessions leading to undesirable unprotected root coverage.

One final retraction method is that disclosed in United States Patent Application Publication No. 2005-0118552-A1, entitled "Gingival Retraction Device and Method", published Jun. 2, 2005, and invented by the inventor of the present application. Disclosed in that application is a device for retracting gingival tissue away from a tooth or plurality of teeth prepared to receive a dental prosthesis comprising a retraction material associated with a provisional restoration to be packed into a sulcus associated with the prepared tooth. The device is preferably compressible, deformably rigid, extensile and non-elastic and will not stick to the gingiva or tooth structure thereby allowing for atraumatic removal leaving a dry open sulcus. A method of use is also disclosed. While that invention was believed to be an improvement over prior retraction methods. It did leave one drawback, namely that it was still an extra step in the process of creating an impression.

There is therefore a need in the art for an improved apparatus for, and method of obtaining an accurate impression, wherein retraction of the gingiva and impression of a tooth abutment or plurality of teeth abutments that have been prepared by drilling or other means to receive a dental restoration (such as a crown, inlay, onlay or implant supported prosthesis) are occur more efficiently while at the same time being no more traumatic than conventional methods (and preferably as atraumatic as possible).

STATEMENT OF THE INVENTION

It is therefore an object of the present invention to provide an improved method of creating a tooth impression.

In one aspect, as embodied and broadly described herein, the present invention provides a method of preparing a tooth for a dental procedure comprising:

(A) removing a portion of the tooth to create a tooth abutment;

(B) providing a dental device having a first retraction/impression material;

(C) placing the dental device containing the retraction/impression material onto the tooth abutment;

(D) exerting pressure on the device to force at least some of the material into a sulcus associated with the tooth, retracting the sulcus;

(E) allowing the retraction/impression material to set;

(F) removing the dental device containing the set retraction/impression material from the tooth abutment, the set retraction/impression material defining a custom impression coping;

(G) separating the custom impression coping from the dental device;

(H) placing the custom impression coping onto the tooth abutment;

(I) exerting pressure on the custom impression coping;

(J) creating an over-impression over the custom impression coping;

(K) removing the over-impression and the custom impression coping from the tooth abutment.

Preferably, the dental device is a preliminary impression having an interior cavity, and providing a dental device having a first retraction/impression material includes placing the first retraction/impression material into the interior cavity of the preliminary impression. It is preferred that before placing retraction/impression material into the interior cavity of the preliminary impression, lubricating the interior cavity of the preliminary impression. The preliminary impression may also be used to create the over-impression over the custom impression coping.

Alternatively, the dental device may selected from the group consisting of a stock tray, a custom tray, a triple tray, a cylinder, a template, a cap, and a tube, which may or may not be lubricated, depending on the device selected.

Removing set material from the custom impression coping may also occur. This will usually be from at least one of a proximal contact area, a distal contact area, and an occlusal area of the custom impression coping, and preferably all.

Preferably, after separating the custom impression coping from the preliminary impression and before placing the custom impression coping onto the tooth abutment, the custom impression coping is relined with a second retraction/impression material. It may preferably be interior cavity of the custom impression coping or outside edge of the custom impression coping that is Mined. Alternatively, after removing the preliminary impression containing the set retraction/impression material from the tooth abutment and before placing the custom impression coping onto the tooth abutment, a second retraction/impression material may be placed in at least a portion, and preferably all, of the sulcus associated with the tooth.

It is preferred that the second retraction/impression material have a hardness that is less than a hardness of the first retraction/impression material. Specifically, it is preferred that the hardness (durometer) of the first material be between 60 c.a. and 120 c.a. inclusive (90 c.a.-95 c.a. being most preferred) and that the hardness (durometer) of the second material be less than 50 c.a. Similarly it is preferred that the second retraction/impression material have a viscosity that is less than a viscosity of the first retraction/impression material.

Creating an over-impression over the custom impression coping may occur while the second material is setting or, alternatively, the second material may be allowed to set. Where the second material is allowed to set and before creating an over-impression over the custom impression, the custom impression coping may be relined with a third retraction/impression material. The characteristics of the third material are preferable similar to those of the second material. In some embodiments, after the second material is allowed to set and before creating an over impression over the custom impression the custom impression coping may be relining with a third retraction/impression material. In some embodiments, it is an interior cavity of the custom impression coping that is relined with the third retraction/impression material. In some embodiments, it is an outside edge of the custom impression coping that is relined with the third retraction/impression material. In some embodiments, after allowing the second material is allowed to set and before creating an over-impression over the custom impression, the custom impression coping may be relined with a third retraction/impression material, and the third retraction/impression material may be placed in at least a portion of the sulcus associated with the tooth. In some embodiments, the third retraction/impression material may be placed in an entirety of the sulcus associated with the tooth.

Where a preliminary impression is not used, at least one item selected from the group consisting of a stock tray, a custom tray, a triple tray, a cylinder, a template, a cap, and a tube, may be used to create the over-impression over the custom impression coping.

The above method of preparing a tooth for a dental procedure may also be adapted to be carried out on a plurality of teeth.

In another aspect, as embodied and broadly described herein, the present invention provides a custom impression coping to be used in a dental procedure for creating a tooth impression to fit a tooth abutment of a tooth, the device comprising:

a body of material having a cavity therein shaped to conform to an exterior surface of the tooth abutment, an occlusal surface, a circumferential surface shaped to allow the body to fit in between teeth next to die tooth in a mouth of a person undergoing the dental procedure, and a portion surrounding an opening of the cavity conforming to the shape of sulcus associated with the tooth when the sulcus is retracted.

What the present inventor has realized is that it is possible to, with the same material, retract the sulcus and create an impression of a tooth abutment, via a custom impression coping. Further, the custom impression coping serves as a precise template and/or vehicle to insert the impression material into the sulcus in a quick and efficient manner. When created, the custom impression coping itself compresses impression material quickly, evenly and precisely and efficiently well beyond the prepared tooth margin, and coincidentally causes retraction of the gingiva as well as expressing fluids such as blood, saliva, crevicular fluid, and debris out of the sulcus.

Pressure is exerted onto a custom impression coping (with or without vibration) by finger pressure or by having the patient bite down on a cotton roll or other object, which is placed on the biting surface, i.e. the "top" of the custom impression coping. Pressure can also be exerted by having the patient close using a "Triple Tray" or "Closed Bite" technique. This causes the thick gel or paste-like material to be precisely expressed into the sulcus and beyond the prepared tooth margin thereby retracting, widening and displacing the gingival away from the tooth margin and coincidentally pushing away or displacing fluids such as blood, crevicular fluid, saliva, and other debris out of the sulcus. Because the custom impression coping conforms intimately to the prepared tooth margin, much in the same way as does a well prepared temporary or provisional restoration, the (hydraulic) pressure exerted by the compressed "custom impression coping" distributes the impression material precisely and equally beyond the prepared tooth margin.

Unlike other compression type retraction methods which cover the tooth abutment as well as the gingival crest (see for example Dragan U.S. Pat. No. 5,676,543) the creation of the custom impression coping does not cover the gingival crest, but rather directs the retraction/impression material directly and more exactly over the tooth abutment into the sulcus and abutment margins and capturing the most important subgingival margins as well as the root structure apical to said margins. As the custom impression coping is very precise, the impression material to which it is associated with, is directed around the abutment and margins in a correspondingly accurate manner and, unlike other "compression-type retraction systems", the impression material is directed apically, the excess being expressed out of the sulcus thereby creating a very atraumatic retraction and impression.

The custom impression coping has a further advantage of being more easily removed (reduced infrabulge and undercuts engaged by the compression—type retraction devices or methods of use) from the abutment(s) so as to be associated with the retraction/impression material device. It can then easily be re-placed over the abutments) so as to be easily relined and replaced back on the abutment. The custom impression coping can be picked up by an over-impression using customary or triple impression trays. It can be constructed easily and quickly and accurately using fast-set materials such as one or any combination of putty, paste, gel, sponge, jelly, foam, cellulose, silicone, plastic, and polyvinylsiloxane, polyether, bis-GMA, acrylics or methacrylates, plastics, thermoplastics. The custom impression coping may be comprised of a stock shell or tube which may be relined using any or a combination of the aforementioned materials. A custom impression coping may have an outer shell which may be rigid or semi-rigid or deformable.

A small vent hole be placed preferably on the occlusal aspect of the custom impression coping.

It is preferred that the custom impression coping be modified before associating it with impression/retraction, in such a way as to polish away or remove some inter-proximal contact surface to allow for impression material from the over-impression, to fill the inter-proximal area of the teeth adjacent to the abutment(s) thereby securing a more accurate impression and thereby producing a dental prosthesis with accurate inter-proximal contacts. The modified custom impression coping can more easily and accurately be re-positioned over the prepared tooth abutment or other dental structure(s) once or numerous times. The impression of the prepared teeth and dental structures can therefore be verified and corrected numerous times before the over impression captures the custom impression coping, thereby eliminating the need to completely re-do an impression if just one little bubble or defect exists. Additionally, impressions of long span splints or bridges can be accomplished in sections followed by an over impression. This greatly increases patient comfort and greatly reduces the gagging reflex and the patient's as well as the dentists' stress.

When a triple tray or closed bite technique is used, it is preferred to reduce the occlusal aspect of the custom impression coping in order to allow for additional impression material to be placed over the occlusal aspect of the custom impression coping, to secure a less distorted and more accurate impression and resultant occlusal fit of the dental prosthesis.

The custom impression coping very accurately captures the most important prepared tooth structures, especially in and around the most critical margin and sulcus. The over-impression then relates the custom impression coping to the adjacent teeth and in the case of a triple tray or closed bite technique, the opposing teeth as well.

The relining as well as the over-impression can compensate for any imprecision found in the re-placing of the custom impression coping in that said modifications will allow impression material over the custom impression coping capturing its relationship with adjacent teeth and other dental structures. A tooth may be prepared for dental procedure via conventional methods to create a tooth abutment having a tooth margin. The margin may be described as a small shelf like area extending from the tooth abutment to the edge of the tooth in the area of the gum line. Generally, the tooth is prepared such that the sulcus is located axially outward from the tooth margin. In order to perform further dental procedures on the tooth, the sulcus must be enlarged such that the gingival tissue is further away from the tooth margin.

The custom impression coping holding the re-lined impression material is then compressed over the prepared tooth abutment, allowing the impression material to be placed over the tooth in the area of the margin and to be packed (forced) into the sulcus distributing evenly and conforming to the prepared tooth margin. Moreover this pressure is even and steady and precise around the margin of the prepared tooth.

The impression material may be associated with the "custom impression coping", as for instance, as a non limiting example, as being placed into the interior of the cavity of the custom impression coping corresponding to the negative form of the prepared tooth abutment. The impression material may be associated with the custom impression coping also as for instance as a non limiting example as being placed on the edge of the margin of the custom impression coping or may first be placed into the sulcus. It is a most preferred that the impression material be placed on the external or outer edge of the margin of the custom impression coping so that as the coping is inserted over the prepared tooth abutment, and the coping is compressed into the sulcus, the inner or proximal wall of the sulcus directs the low viscosity, low durometer reline impression material apically to capture the margin of the abutment.

The present invention overcomes the deficiencies of the prior art in several respects. The custom impression coping serves as a precise template and/or vehicle to insert the impression material into the sulcus in a quick and efficient manner. It compresses the impression material quickly, evenly and precisely and efficiently well beyond the prepared tooth margin, and coincidentally, causes retraction of the gingiva as well as coincidentally expressing fluids such as blood, saliva, crevicular fluid, and debris out of the sulcus; this retraction/impression material is held solidly in the sulcus by the custom impression coping during the entire impression period. This is an improvement over other impression methods which require the pushing of cords and rings with small dental instruments into the sulcus which is time consuming, tedious, inefficient and traumatic often causing bleeding and ejection of the cord from the sulcus on one side as the other side is pressed down. The tongue and cheek and saliva, suction tubes, often dislodge or wash away cords or pastes. Thus, packing of the sulcus in the same area several times, and the tearing and/or abrasions associated therewith are minimized or avoided. Mutilation of the gingival tissue is avoided. Retraction and therefore the need to wash and dry the sulcus prior to impression taking is eliminated. Therefore, this additional step, which can lead to bleeding or oozing from the sulcus, is eliminated.

It should be noted that retraction and simultaneous impression occurs firstly during the stage of the fabrication of the custom impression coping from preferably a preliminary impression as well as preferably during the second stage of the re-lining and the re-placement of said impression coping.

Moreover, the retraction/impression material of the present invention is easy to handle and to place, is inexpensive, precise and efficient and can be used for single or multiple restorations. It does not adhere to the gingiva nor tooth abutment. It is held in place securely by the custom impression coping.

Finally, the retraction/impression material of the present invention allows for faster, more accurate and less damaging gingival retractions, leading to better results from the dental procedures (e.g. preparing a crown) that they are intended to facilitate.

The retraction/impression material of the present invention is a semi-solid or a thick gel or silicone or putty type of material or a material or a paste which transforms or hardens or sets into a semi solid or gel and is of a consistency that it compresses into the sulcus and beyond the prepared tooth margin thereby retracting, widening and displacing the gingival away from the tooth margin and coincidentally pushing and expressing away or displacing fluids such as blood, crevicular fluid, saliva, and other debris out of the sulcus.

As used in the context of the present specification, the term "retraction/impression" material is intended to include any material whether single or in any combination of a solid, semisolid or liquid, which as a non-limiting example may be in the form of a putty, gel, gelatine, paste, silicone, polyvinylsiloxane, polyether, methacrylate, bis GMA or other. The retraction/impression material may harden or set.

The retraction/impression material can be used to retract tissues and tab an impression around a singular prepared tooth abutment or a plurality of tooth abutments. It should be understood that since each human has several different types of teeth, each being of different size, and that since the size of the same type of tooth will vary between humans, the impression material fills the interior of the custom impression coping which has been accurately and custom fit to the tooth or teeth abutments and therefore will be of the ideal size, amount, accuracy, precision to retract the sulcular tissues adjacent to the gingival margin or margins as well as obtain a very accurate and precise impression. It should also be noted that the retraction/impression material can be made to harden or set at variable speeds and consistencies to retract the sulcus around a variety and number of teeth and impress said tooth or teeth abutments. For example the impression material can be made to harden or set more slowly to allow for more time (working time) to fill and place the custom impression coping over a plurality of teeth.

It is highly preferable that the retraction/impression material be compressible. The consistency of the retraction/impression material should be able to be placed into the interior of preliminary impression or other template, and not run out when the preliminary impression or template is inverted and then placed on the tooth abutment. It is preferable that the retraction/impression material will displace the saliva and blood and other fluids and debris out of the sulcus as it is compressed over the abutment by the preliminary impression or template. Deformability is highly desirable as the retraction-impression material must flow along the top and axial contours of the tooth abutment and then down into the sulcus. The retraction/impression material can be expansile. The retraction/impression material should be resistant to tearing while being deformed. Once deformed it should retain its new shape. It should not tend to return to its original pre-deformation shape because this impedes gingival tissue retraction and creates inaccurate impressions.

Further, it is highly preferable that the custom impression material be deformably rigid when set. In order that the custom impression material be easy to work with, when modifying or when re-placing it into the sulcus, the custom impression material should partially retain its shape (not deform) under forces less than the amount necessary to compress it into the sulcus. In this manner, the custom impression material will be able to be removed easily from the prepared tooth abutment and the patient's mouth.

More preferably the custom impression material can be a mixture of equal quantities of regular set or fast set impression material which may contain any combination of, but not limited to, fillers, fibers, modifiers.

Where the custom impression material comprises more than one material, it may comprise either a homogenous mixture of materials or separate and distinct layers of different materials or mixtures of homogenous materials. In such cases the custom impression material may comprise a thin layer of a fluid-impervious material (e.g. akin to the barrier layer of a conventional sanitary napkin), and a layer of retraction material of a sponge, gel, jelly, foam, putty, cellulose, polyvinylsiloxane, silicone, plastic, paste. (e.g. the described hereinabove). The previous described web of material may comprise several different types of layers. By way of non-limiting example, the layers may be a fibrous layer, a paste layer, and gelatinous layer.

It should be understood that the custom impression material may contain or be dipped or soaked or otherwise impregnated with or otherwise contain or carry other medical ingredients without departing from the scope of the present invention. By way of non-limiting example, such ingredients may be astringents, antiseptics, antibiotics, and hemostyptics.

The custom impression material of the present invention may be manufactured by any conventional means appropriate for the materials of which they are constructed. As a non-limiting example, the custom impression material may be formed by mixing a powder and a liquid or a paste and a paste, or a paste and a liquid or a paste and a powder, or a gel with one or more of the aforementioned. The constituents may be mixed either by hand or in a mixing device such as but not limited to an automixing chamber ("automixing gun" or "automixing syringe") or in a capsule which is then triturated or mixed in a dental triturator. By way of non-limiting example, the components may be contained in separate compartments of a dental capsule and then activated (the internal membrane is punctured allowing the components to be mixed) and then triturated in a dental triturator. This capsule can have a nozzle through which the mixed retraction material can be inserted into the interior of the temp. The custom impression material may be made of one or a combination of materials which do not require mixing but have some or all of the necessary properties as aforementioned. The custom impression material may harden or set simply by being exposed to air and/or moisture.

Whatever the composition of the material, it is preferred that the material be compressible in use. The material should be able to be compacted while the custom impression material is being compressed and packed into the sulcus, and in this manner, the material will be under pressure once forced therein. The pressure caused by the compressed state of the material will aid in forcing the salcus to expand and retracting the gingival tissue. An additional benefit of the compression of the custom impression material on the sulcular tissue is to produce hemostasis. It may also be desirable that the material be somewhat absorbent so that fluids being exudated from the body into the sulcus are contained and maintained away from the tooth where they could negatively interfere with the dental procedures to be performed. Further absorbent materials generally tend to increase in size as they absorb, thus in the present case, increasing the amount of pressure on the gingival tissue and thereby the retraction and hemostasis.

The relined impression material which is held in place securely by the custom impression coping prevents displacement by any or any combination of the patients tongue, cheek, saliva, dental instrument; the custom impression coping allows for additional retraction to be achieved by further compressing the impression material deeper and more precisely into the sulcus. The custom impression material can be of a consistency that allows it to be withdrawn from sulcus atraumatically and withdrawn as easily as a provisional or temporary is withdrawn from the prepared tooth abutment.

The custom impression coping which is comprised of a retraction/impression material may harden or set. The hardening or setting of the retraction material may occur chemically or by the elapse of time or by light activation.

The retraction/impression material may be resistant to tearing while being deformed. Once deformed it should retain its new shape. It should not tend to return to its original pre-deformation shape because this impedes gingival tissue retraction. The retraction/impression material may preferably be deformably rigid; the retraction material should partially retain its shape (not deform) under forces less than the amount necessary to compress it into the sulcus.

The retraction/impression material preferably may be constructed preferably from one (or more) selected from the group consisting of: putty, cellulose, polyvinylsiloxane, polyether, silicone, plastic, powder/liquid mixture, or paste.

Preferably the retraction/impression material can be a mixture of regular set or fast set impression material base and catalyst which may contain any combination of, but not limited to, fillers, fibers, modifiers.

In addition, it is highly preferred that the material be atraumatically removable from the sulcus. Ideally, the material should not have any component that bonds to either the gingival tissue or the tooth making removal of the retraction material difficult or causing damage to either. Ideally, the retraction material should be able to be removed from the sulcus as simply as it was inserted via being pulled out by withdrawing the custom impression coping with a forceps type of dental instrument.

In another aspect, as embodied and broadly described herein, the present invention provides a method of preparing a tooth for a dental procedure comprising the steps of: obtaining a preliminary impression or stock or custom template of the unprepared tooth; removing a portion of a tooth to create a tooth abutment; lubricating the interior aspect of the preliminary impression or template; placing retraction/impression material as described hereinabove into the cavity of a preliminary impression or stock or custom template and re-placing said lubricated preliminary impression containing the retraction impression material within the cavity(s) corresponding to the tooth abutment(s) or packing the retraction/impression material into a sulcus associated with the tooth and re-placing the lubricated preliminary impression over the abutments; exerting apical pressure on the preliminary impression or template filled with "retraction/impression" material and allow same to set or harden; removing the preliminary impression or template, containing the set retraction impression material, which now comprises the custom impression coping, simply and atraumatically from the sulcus; separating the custom impression coping from the preliminary impression and rinsing both thoroughly; modifying the custom impression coping by removing excess material and stripping the proximal and distal inter proximal contact areas as well as the occlusal aspect of the tooth or teeth to be restored; relining the custom impression coping with a low viscosity, low durometer impression material, preferably only on the margin of the custom impression coping, and more preferably only on the external aspect of the margin of the custom impression coping; re-placing back said custom impression coping onto the corresponding tooth or teeth abutments with slight finger pressure; adding additional low viscosity impression material to the areas of the custom impression coping which were modified, for instance the interproximal and occlusal aspects of custom impression coping as well as the occlusal aspect of the preliminary impression; taking an over-impression of the custom impression coping using said preliminary impression and the impression material is allowed to set; atraumatically removing the over impression containing the relined custom impression coping.

Preferably, once the tooth has been prepared to create a tooth abutment, a custom impression coping is prepared in a manner identical to the fabrication of a temporary or a provisional crown or bridge restoration using preferably a harder durometer polyvinylsiloxane or other materials aforementioned. The retraction impression material has been placed into the cavity of the preliminary impression or template; the custom impression coping is then placed on top of the prepared abutment. Occlusal pressure exerted and will cause the retraction/impression material to be forced into the sulcus all around the tooth neatly simultaneously and to conform to the irregularities of the prepared tooth margin. Should the patient have no tooth opposing the provisional restoration a relatively large cotton wad may be placed thereon (enabling the patient to bite down) or alternatively, the dental practitioner may apply manual pressure. When using a triple tray or closed arch impression technique the patient is instructed to bite their teeth together thereby exerting adequate occlusal force to obtain both tissue retraction and impression of the abutment.

It is most preferred that the retraction impression material can simply be placed into the cavity of the preliminary impression with a spatula or dental instrument or automixing gun or syringe. Or, the retraction/impression material can be injected into the sulcus with a simple syringe, i.e. CR syringe or auto syringe and then the preliminary impression can be placed over the retraction/impression material thereby compressing it into the sulcus and simultaneously obtaining an impression.

It is most preferred that once the tooth has been prepared to create a tooth abutment, a custom impression coping is prepared. The retraction/impression material is then adhered to the gingival margin, but slightly adhesive to the preliminary impression (having the retraction/impression material adhered thereto) and is placed on the tooth and pressure (finger pressure or vibration exerted in an apical direction) is exerted onto the custom impression coping. The occlusal pressure thus exerted will cause the retraction/impression material to be forced into the sulcus all around the tooth nearly simultaneously.

It is most preferred that after the custom impression coping associated with the retraction/impression material is compressed over the prepared tooth abutment, an impression tray filled with unset impression material is placed over the custom impression coping (filled with retraction/impression material which has already set or is still unset) and allowed to set. The custom impression coping containing the set retraction/impression material is now associated with and embedded in the over impression contained in the tray. The impression tray is removed containing the custom impression coping thereby securing a very precise impression of the tooth abutment(s), as well as the adjacent teeth and oral structures.

In all cases, the over impression mentioned herein may apply to any but not limited to a list of a stock tray, custom tray, triple tray, preliminary impression tray, or a preliminary impression tray with a spacer.

A custom impression coping which may be composed of but not limited to either or any combination of cotton, polyvinylsiloxane, polyether, polypropylene, polyethylene, polystyrene, cement, bis-GMA composite or other composite, methyl methacrylate or other methacrylate.

The custom impression coping can be made in a manner similar to making a provisional temporary, i.e. from a preliminary impression taken before the tooth abutment is prepared. It is preferable to place a separating medium between the set preliminary impression and the material which makes up the custom impression coping. This separating medium can be a separating medium including but not limited to microfilm, PAM™ vegetable spray or a layer of ultra thin plastic or aluminium film.

In a preferred embodiment of this custom impression coping, the inter-proximal contours may be reduced allowing for easy seating and less binding and resultant distortion. This can be accomplished by slicing away the inter-proximal contours with a scalpel blade if a softer material such as PVS or silicone type material is used is used, or grinding away the inter-proximal contours with a diamond or stone or wheel. The impression material from the over-impression fills the gap between the custom impression coping and the adjacent teeth thereby securing an accurate impression of the adjacent teeth.

In a moat preferred embodiment of the custom impression coping, a tube like matrix or mini impression holder may be filled with one or more but not limited to either or any combination of cotton, polyvinylsiloxane, polyether, polypropylene, polyethylene, polystyrene, cement, bis-GMA composite or other composite, methyl methacrylate or other methacrylate. This tube may be then placed over each abutment and compressed to obtain a template or negative or impression of the tooth abutment and its margin. When this custom impression coping is filled with a retraction/impression material, the custom impression coping serves as a precise template and/or vehicle to insert the impression material into the sulcus in a quick and efficient manner. It compresses the impression material quickly, evenly and precisely and efficiently well beyond the prepared tooth margin, and coincidentally causes retraction of the gingiva as well as coincidentally expressing fluids such as blood, saliva, crevicular fluid, and debris out of the sulcus.

In the above paragraphs, the present invention has been described in terms of a single tooth. It is, however, within the scope of the present invention that a retraction device be constructed for use with more than one tooth. Thus, as embodied and broadly described here, the present provides a device for retracting gingival tissue away from a plurality of teeth, the device comprising a retraction/impression material to be packed and compressed into a sulci associated with a single or plurality of teeth. As a non-limiting example the retraction/impression material can have a longer working time or setting or hardening time to allow additional time to fill the cavities of a plurality of teeth, to place the custom impression coping on the abutments, and compress the custom impression copings in a gingival direction extruding the retraction/impression material into the sulcus.

In this aspect the retraction/impression material described hereinabove is inserted into the abutment cavities of the custom impression coping made to impress a plurality of prepared teeth. This structure may be used when more than one tooth is being prepared for a dental procedure. The dental practitioner simply inserts the retraction/impression material into each of the custom impression copings cavities and places the custom impression copings over the abutment teeth thereby compressing the retraction/impression material into the sulci of the plurality of prepared teeth. Removal of the device is simply the reverse of this process.

It is important to note that it takes only a few seconds longer to retract the gingival and obtain an impression around a plurality of teeth (up to 16 teeth) using this method as it takes for one tooth thereby saving significant time and expense.

An embodiment of the present invention can consist of many various compositions and consistencies. It is a preferred embodiment of the initial retraction/impression material to be of a consistency which will help to extrude fluids and debris out of the sulcus and atraumatically compress said sulcus apically and laterally while simultaneously capturing an accurate impression of the margin of the prepared tooth abutment after said retraction/impression material sets.

As with any impression material or technique, bubbles or debris or liquid or incomplete retraction may cause voids or distortions especially around the most important margin area of the prepared tooth abutment. The entire impression process including retraction many times would have to be repeated from the beginning wasting much time and creating more trauma to the gingival and particularly the fragile sulcular area. Some have attempted to reline the faulty impression and reposition said impression back over the prepared abutment. Because of the many contours and infrabulge and undercut areas of said faulty impression, it is virtually impossible to re-seat accurately said impression back over the tooth abutment as well as the other teeth.

The custom impression coping containing set retraction impression material however can easily be relined with a more fluid or lighter bodied embodiment of the present invention and precisely re-seated over the prepared tooth abutment generating an accurate corrected impression.

As an additional embodiment of this present invention, a more fluid lighter bodied retraction/impression material may be applied to the external aspect of the margin of the set heavier bodied retraction/impression material. A tiny drop of this lighter bodied retraction/impression material can be placed only on the bubble or faulty part of an initial impression while preserving the zest of the impression. It should be noted that it is preferred that the lighter bodied retraction/ impression material should be placed on the exterior aspect (adjacent to the exterior wall of the sulcus, rather than adjacent to the axial wall of the prepared tooth abutment) of the margin. As the custom impression coping is reseated, the light bodied retraction material is compressed apically deflecting the sulcus in a lateral and apical direction and said material is coincidentally directed by the boundaries of the inner wall of the sulcus and the axial wall of the prepared tooth abutment.

It may be desirable to obtain a more precise impression of the margin of the prepared tooth in which case the entire circumference of the gingival margin of the set embodiment of the present invention may be relined in a similar manner.

The present invention provides enhanced results with much greater precision, predictability and ease for the dentist. It uses less material and is more cost efficient, Additionally, the present invention decreases the gagging reflex and provides much greater comfort for the patient. Defects, bubbles, imperfections and missed impression detail can be quickly and easily corrected, without having to re-take the entire impression. Accordingly the present invention greatly advances the art of dentistry.

While the present invention has been described with respect to various embodiments, various modifications may be made without departing from the spirit or scope of this invention. Other objects and features will become apparent by reference to the following description and the drawings.

BRIEF DESCRIPTION OF THE DRAWINGS

A detailed description of preferred embodiments of the claimed invention is provided herein below, with reference to the following drawings, in which:

DETAILED DESCRIPTION OF PREFERRED EMBODIMENTS

Figure 1A:
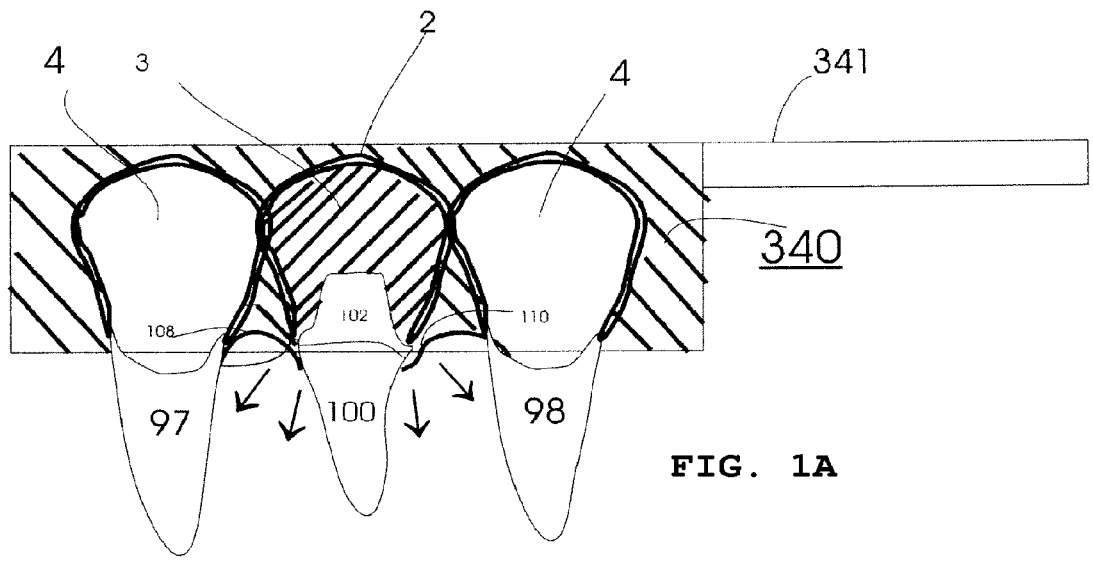
FIG. 1a is a longitudinal section illustrating the fabrication of custom impression coping from a preliminary impression.

FIG. 1a illustrates the fabrication of a custom impression coping 2 which has been fabricated by placing an unset retraction/impression material 3 into a set or hardened preliminary impression 340, which has been fabricated by taking an impression of the tooth to be prepared 100 including the adjacent teeth 97 and 98, using an impression material contained in an impression tray 341. The unset retraction-impression material 3 has been placed into the cavity 2 corresponding to the prepared tooth abutment 102 of the preliminary impression 340 and then the impression tray 341 is replaced back over the teeth compressing the unset retraction/impression material 3 over the prepared tooth abutment 102 and into the sulcus 110, thereby capturing the form of the abutment 102, the abutment margins 104 and 105. The retraction/impression material 3 is placed only in the cavity corresponding to the prepared tooth abutment 102. The cavity 4 of the adjacent teeth is not filled with the retraction/impression paste 3 so that the hardened preliminary impression 340 can be easily replaced back over the abutment 102 and adjacent teeth 97 and 98. The retraction/impression material 3 is allowed to set and the impression tray 341 is removed from the mouth and the set retraction-impression material which now forms the custom impression coping is removed from the preliminary impression 340.

Figure 1B:
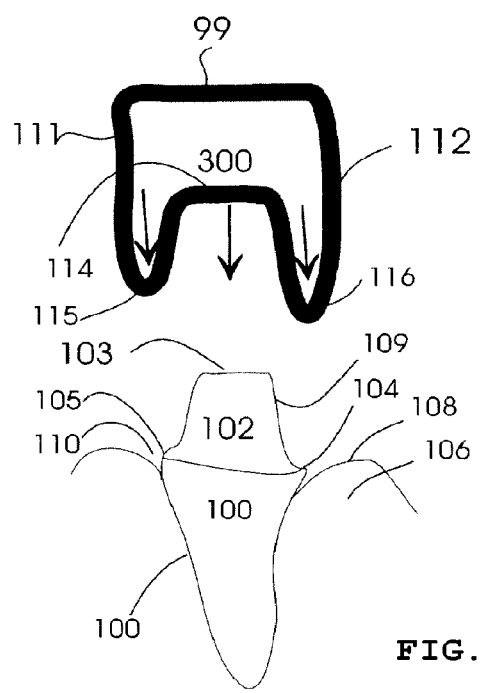
FIG. 1b is a longitudinal cross-sectional view of a human tooth prepared to receive a custom impression coping of the present invention.

Referring to FIG. 1b there is illustrated a human tooth 100 that has been prepared for a dental procedure by conventional means. Specifically the surface tooth structure of the tooth 100 has been removed creating a tooth abutment 102 having a tooth margin 104, 105. The tooth 100 is embedded in gingival tissue 106 having a gingival crest 108. Between the gingival tissue 106 and the tooth 100 is located a sulcus 110. A custom impression coping 300 (similar to custom impression coping 2 but different in shape) has been fabricated using an embodiment of the present invention consisting of unset retraction-impression material which has been inserted into the corresponding cavity of a set, lubricated preliminary impression, of an unprepared tooth.

The preliminary impression is then seated onto the abutment 102 and the retraction-impression material simultaneously retracts the gingival and obtains an accurate impression of the entire tooth abutment 102, and is allowed to set. The set retraction-impression material now comprised the custom impression coping 300. The custom impression coping is then easily removed from the lubricated preliminary impression. The proximal 111 and the distal 112 surfaces of the custom impression coping are cut or polished so as to be flat or slightly convergent occlusally so as to allow for easy unencumbered withdrawal and in placement onto the tooth abutment. The occlusal aspect 99 of the custom impression coping is also reduced so as to allow for clearance for an over impression using a triple tray or closed bite technique or preliminary impression and thereby prevent distortion.

A custom impression coping 300 has been fabricated from a dental impression to register with the prepared tooth 102. The custom impression coping 300, which has a form very similar to an accurately fitting temporary or provisional restoration, has an interior surface 114 and a distal margin 116, and a mesial margin 115 that are together configured to conform to the tooth abutment 102 and the mesial tooth margin 105 and the distal tooth margin 104 respectively. As can be seen in the drawings the preparation of the tooth 100 and thus the custom impression coping 300 may not be symmetric about the center of the tooth 100.

Figure 2A:
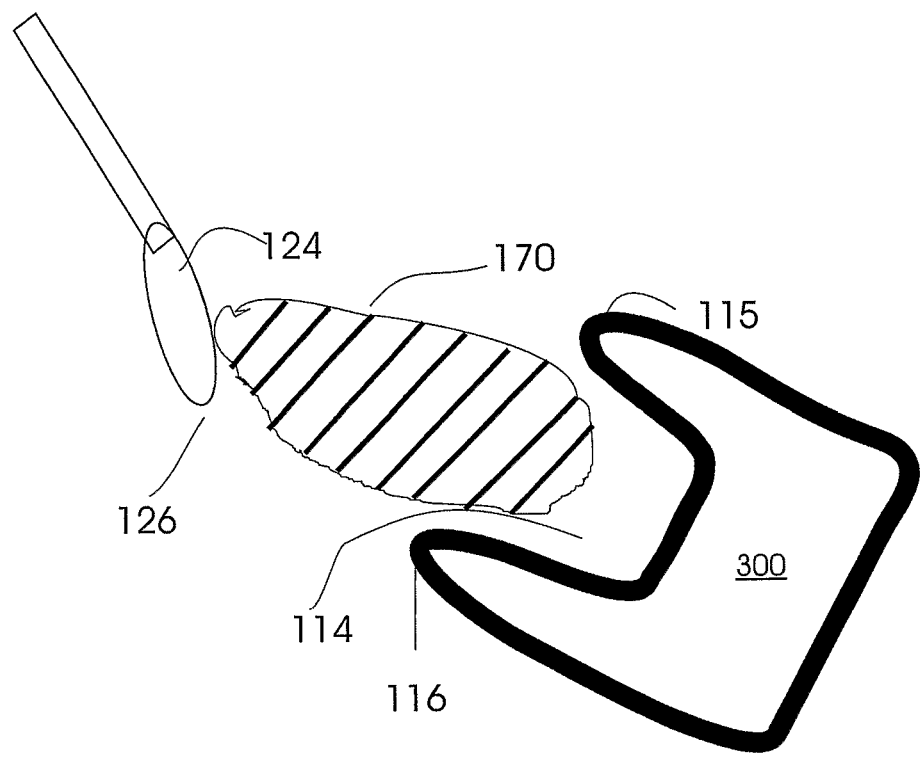
FIG. 2a is a longitudinal cross-sectional view of retraction/impression material of the present invention being placed into the cavity of the custom impression coping.
Figure 2A:
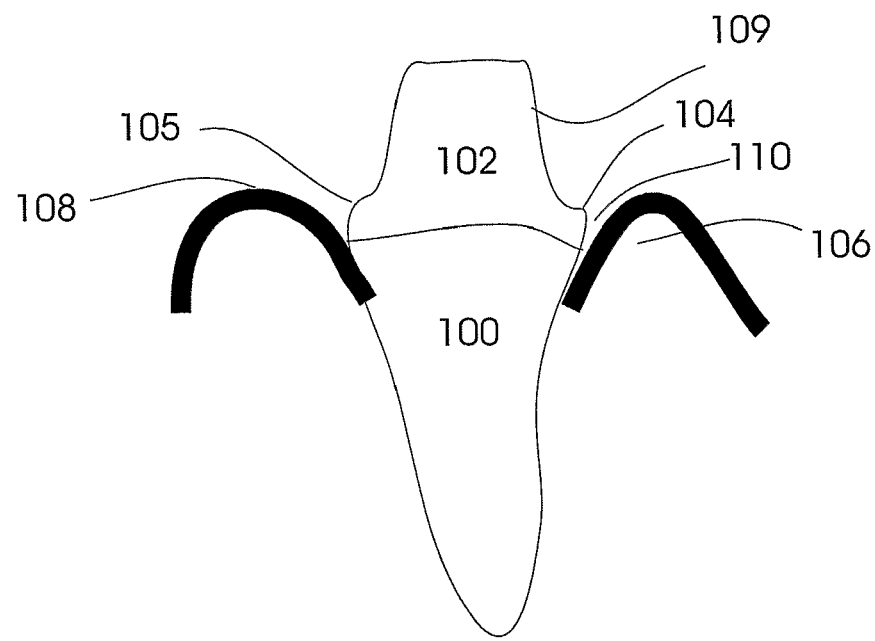
Figure 5:
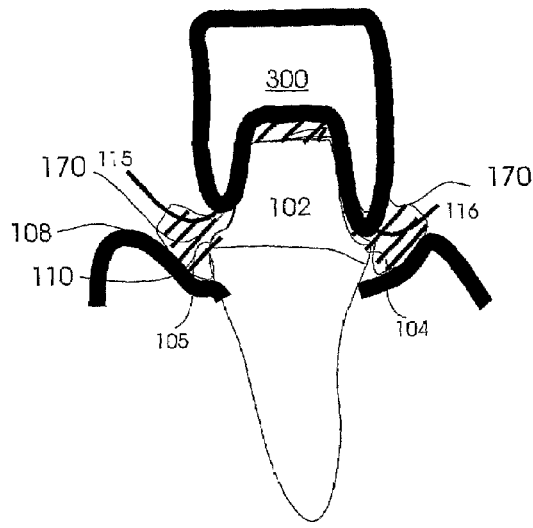
FIG. 5 is a longitudinal cross-sectional view of a human tooth as in the prior figures later in time illustrating the packing of a retraction/impression material into a sulcus associated with the tooth via the compression of the retraction/ impression material by the custom impression coping; the material expressing and displacing fluids and debris out of the sulcus and displacing the gingival tissues in an apical and lateral direction and simultaneously capturing preferably an accurate impression of the tooth abutment as well as the root surface apical to a prepared margin.

Referring to FIG. 2a, there is shown retraction material 170 of the present invention. The retraction impression material 170 is placed into the cavity of the custom impression coping 300 against the interior surface, 114 with the blade 126, of the dental instrument 124. Care is taken to overfill the cavity of the custom impression coping 300 to ensure proper retraction and impression. The overflow will gently and atraumatically deflect and spill out of the sulcus as seen in FIG. 5. The retraction material can be inserted by way of a syringe type apparatus (not shown) as for instance but not limited to an automix syringe.

Figure 2B:
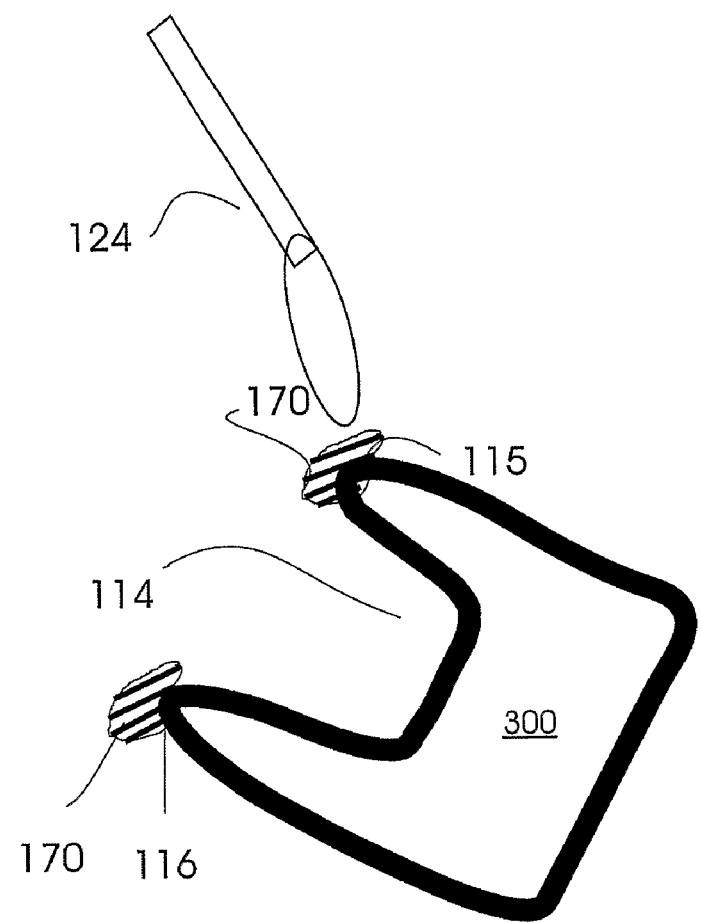
FIG. 2b is a longitudinal cross-sectional view of retraction/impression material of the present invention being placed onto the outer edges of the cavity of the custom impression coping.
Figure 2B:
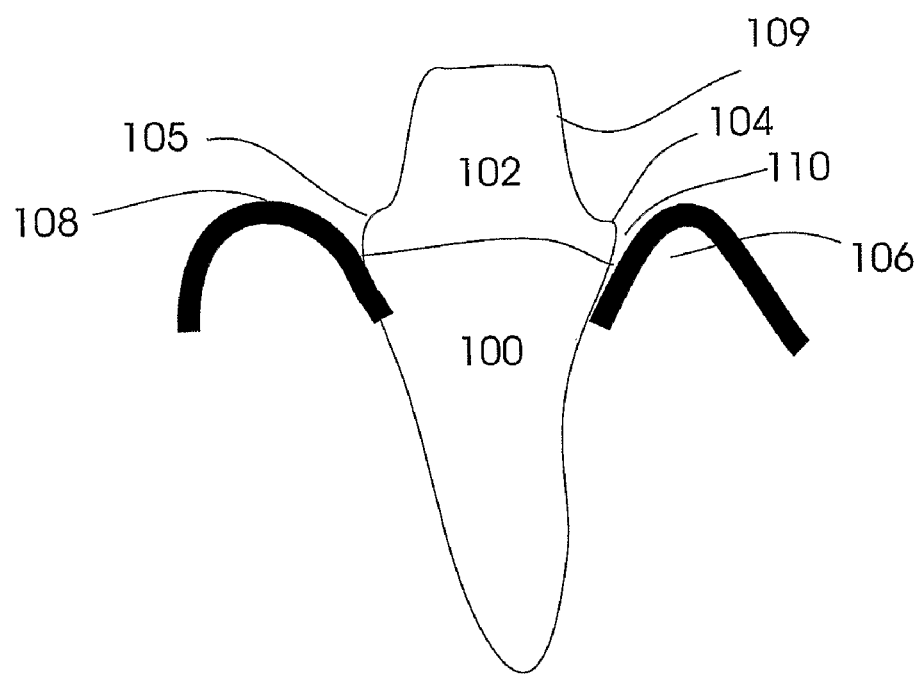

Referring to FIG. 2b, an alternative method of use is shown as the retraction-impression material 170 is placed onto the gingival margins 115 and 116 of the custom impression coping 300.

Figure 3:
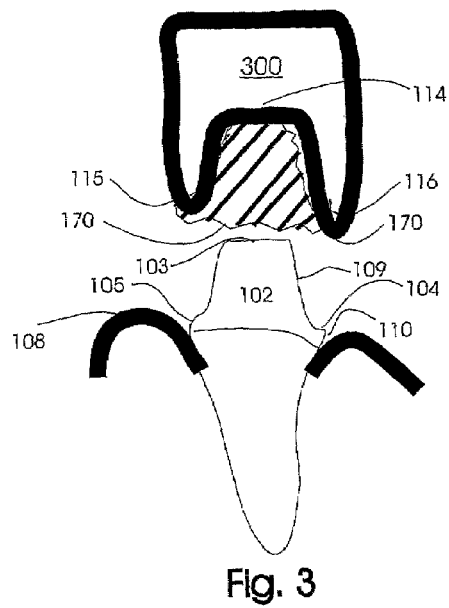
FIG. 3 is a longitudinal cross-section of the custom impression coping shown in FIG. 2 having a cavity having retraction/impression material therein immediately before being inserted onto a prepared tooth abutment.
Figure 4:
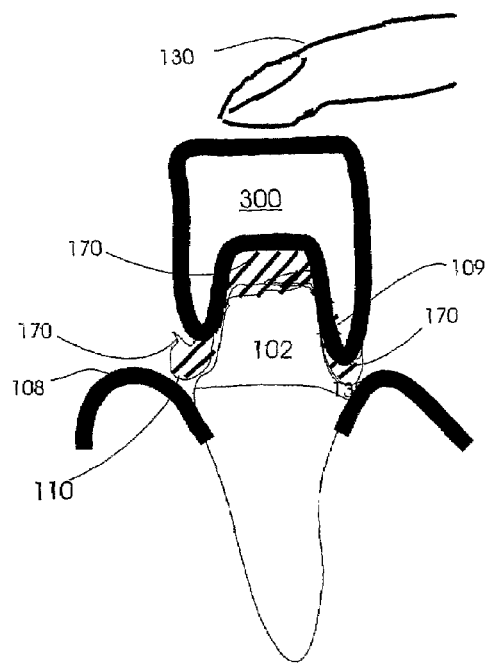
FIG. 4 is a longitudinal cross-sectional view of a human tooth as in the prior figures later in time illustrating the compression and flow of retraction/impression material along the axial surface of the prepared tooth abutment in an apical or gingival direction as the result of the exertion of pressure on the custom impression coping.

Referring to FIGS. 3, 4, retraction impression material 170, contained in the custom impression coping 300 has been placed over the tooth abutment 102 with thumb or forefinger 130 or a dental clamp or forceps (not shown). Attention is taken to place the custom impression coping 300 over the middle of the abutment 102 so that the retraction impression material will be compressed uniformly.

Referring to FIG. 4, finger pressure 130 is exerted to compress the retraction impression material over the tooth abutment 102 along its axial walls 109. The retraction impression material 170 is compressed and extruded along the axial walls 109 of the abutment 102 moving in an apical direction towards the sulcus 110.

Figure 6:
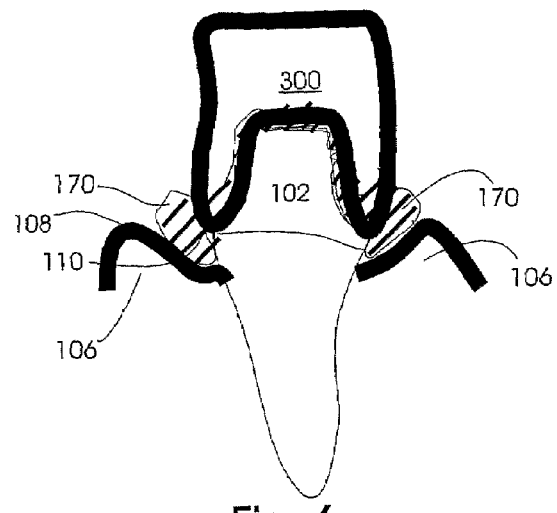
FIG. 6 is a longitudinal cross-sectional view a human tooth as in the prior figures later in time illustrating the apical flow of the retraction/impression material achieved by further compression of the custom impression coping, with the excess of retraction/impression material being directed and extruded out of the sulcus preferably providing atraumatic retraction and impression of the tooth abutment and decreasing tearing and irritation of the sulcus.

Referring to FIG. 5, the patient is then asked to bite down on the custom impression coping 300, and as shown in FIGS. 5-9, the occlusal force exerted by the patient causes the retraction impression material 170 to be forced into the sulcus 110 nearly simultaneously and precisely around the entire circumference of tooth 100. In doing so, it is possible (as is shown in FIGS. 5 and 6) that a portion of the retraction material 170 will remain between the custom impression coping margin 116 and the tooth margin 104. This portion 170 serves to anchor the retraction impression material 170 and more precisely capture the gingival margin and beyond. The overflow will gently and atraumatically deflect and spill out of the sulcus.

As shown in FIG. 6, if the retraction of gingival tissue 106 is insufficient after the custom impression coping 300 has caused the retraction material 170 to be packed in the sulcus 110. The practitioner may cause additional packing through the application of manual force on the retraction impression material via a dental instrument (not shown). This will cause more of the retraction impression material 170 to be packed in the sulcus 110 providing additional retraction. A significant advantage of using the custom impression coping to hold down the retraction impression material without being dislodged as the retraction impression material is being compressed into the sulcus is clearly demonstrated.

Figure 7:
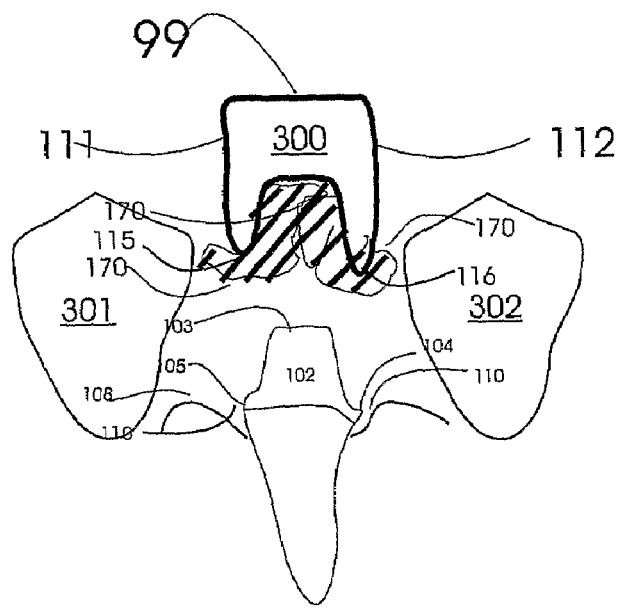
FIG. 7. is a longitudinal cross-sectional view similar to FIG. 3 illustrating teeth adjacent to the prepared tooth abutment and a custom impression coping filled with retraction/ impression material being placed over the prepared tooth abutment.
Figure 8:
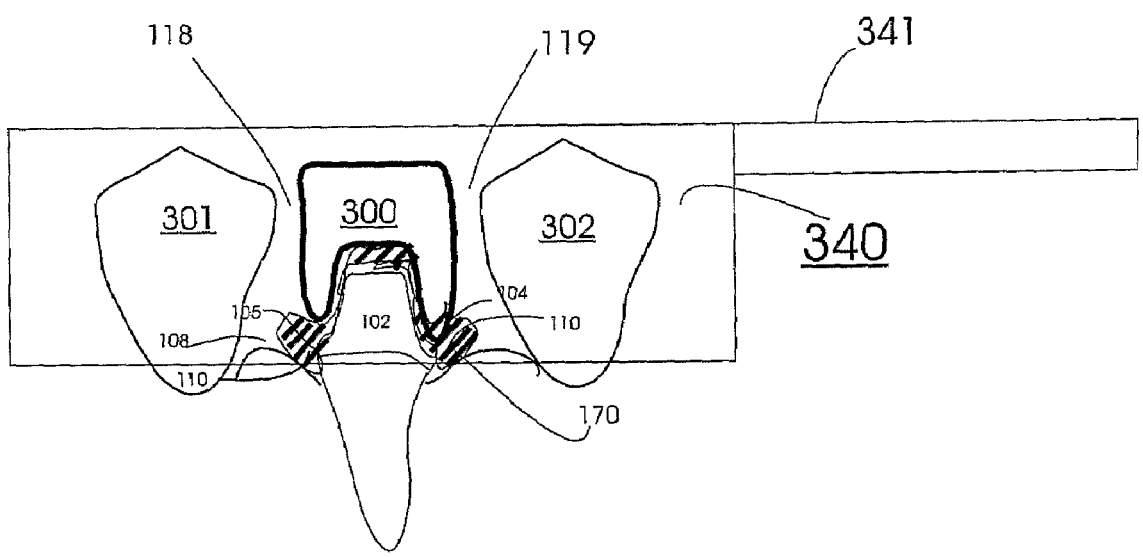
FIG. 8 is a longitudinal cross-sectional view similar to FIG. 3 illustrating a custom impression coping filled with retraction/impression material which has been compressed over the prepared tooth abutment and teeth adjacent to the prepared tooth abutment and an impression tray filled with impression material which has been inserted over said custom impression coping and adjacent teeth.

FIG. 7 illustrates how the custom impression coping 300 is placed over the tooth abutment 102 and the modification of said custom impression coping so that the proximal contact area 111 and the distal proximal area 112 have been reduced to eliminate the infrabulge contour so as not to bind against the adjacent teeth 301 and 302, and to allow for unset impression material from an over-impression as seen in FIG. 8 to flow into the proximal 118 and distal 119 spaces so as to accurately capture the contact areas. Similarly the occlusal 99 aspect of the custom impression coping 300 is reduced to allow for clearance when a "closed bite" or "triple tray" technique is used.

FIG. 8 illustrates how the retraction material 170 is directed towards the margins of the prepared abutment 102 by the custom impression coping 300. The unevenness and asymmetry of the abutment margin is seen as the mesial abutment margin 105 is located more occlusally (higher) than the distal abutment margin 104 which is located more apically (lower). Because the custom impression coping 300 was fabricated to fit precisely the abutment margin of the prepared tooth, the distal margin of the custom impression coping 300 corresponds to the distal margin of the abutment 104 and similarly the mesial margin of the temp 115 corresponds to the mesial margin of the tooth abutment 105. With other retraction devices, it would be far more difficult to retract and take an impression of abutment margins which are located more subgingivally as evidenced by the distal abutment margin 104. Once the retraction material is inserted into the internal cavity 114 custom impression coping 300 and is compressed by the temp along the tooth abutment, the retraction material 170 is expressed precisely beyond (apical to) the abutment margin filling the sulcus 110. An embodiment of this invention 170 is illustrated as being associated with the custom impression coping 300 and is compressed over the tooth abutment 102, after which an over impression 341 covers the custom impression coping 300 and the retraction-impression material 170 as well as the adjacent teeth 301 and 302, and the impression material 340 contained in the over impression tray 341, captures the space proximal 118 and distal 119 to the custom impression coping 300, and is allowed to set thereby atraumatically picking up the custom impression coping 300 when the over impression is removed. It should be noted that the retraction/impression material 170 can be allowed to set or can be in an unset form as the over impression is placed over the custom impression coping 300.

Figure 9:
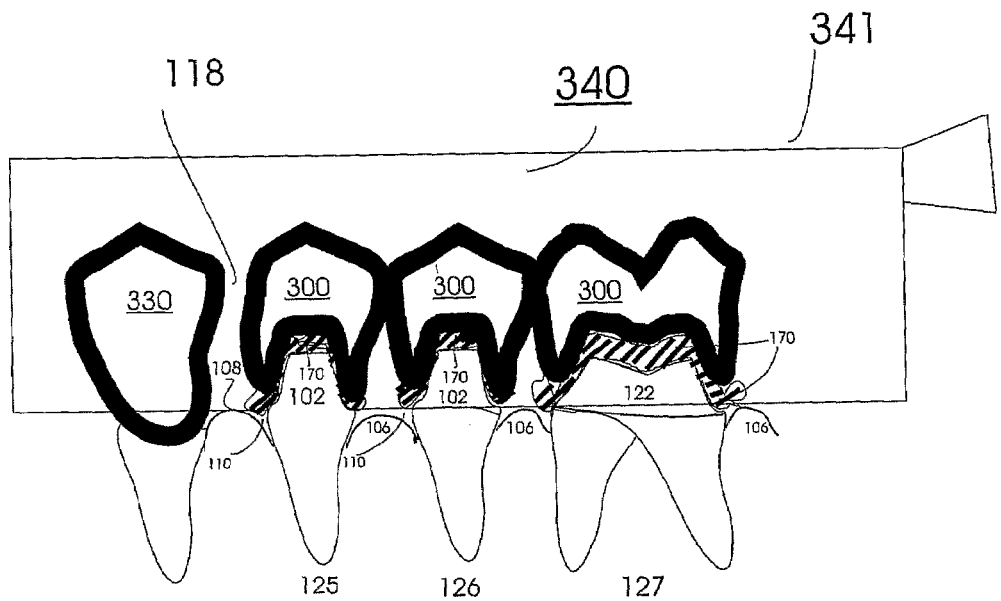
FIG. 9 is a longitudinal cross section view of an embodiment of a device of the present invention suitable for use with a plurality of teeth, illustrating the effective, continuous, retraction and impression of the sulci and margins of the plurality of teeth on the facial and lingual as well as interproximal aspects.

FIG. 9 illustrates a plurality of tooth abutments which can be but are not limited to be individual or splinted together, or can correspond to a bridge (if the middle tooth 126 were missing, for example). It illustrates the low viscosity retraction impression material 170 filling and compressing the gingival sulcus 110 of a plurality of teeth 125, 126, 127. As pressure is placed on the top of the custom impression coping 300 by the apical pressure exerted by the unset over impression material 340 held in the tray 341, the retraction impression material 170 compresses further into the sulcus 110 firmly yet gently and atraumatically, and overflows the sulcus 110 thereby minimizing excessive and potentially harmful manipulation and trauma of the sulcus 110. Both retraction and impression are accomplished in one step safely, quickly, efficiently, precisely and predictably.

Figure 10:
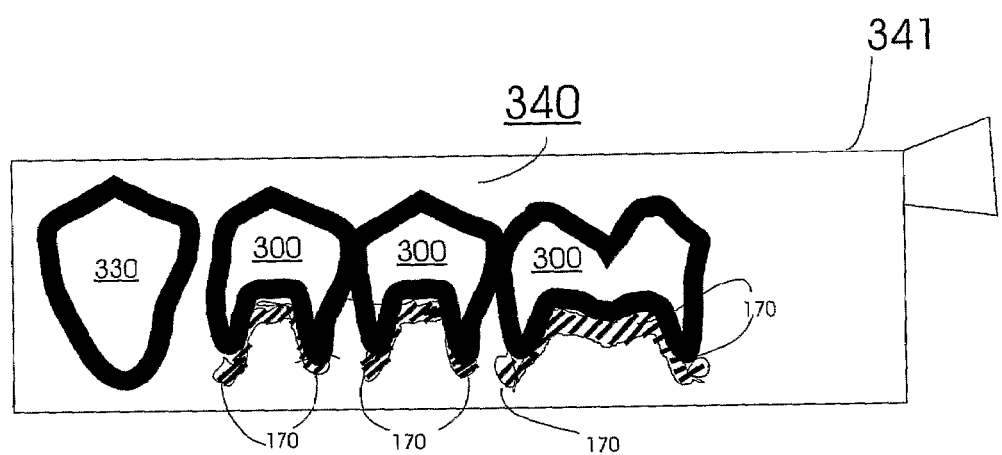
FIG. 10 is a longitudinal cross section view of an impression tray holding the set impression containing (capturing the precise likeness of) a plurality of the prepared tooth abutments as well as the adjacent teeth.

FIG. 10 illustrates the atraumatic removal of the retraction-impression material 170 as it is attached to and coincidentally, withdrawn with the custom impression coping 300 producing efficient complete and precise retraction and coincident impression of the prepared teeth. Note that the retraction/impression material does not stick to the gingiva 106 nor the tooth abutment 102 but sticks onto the interior of the custom impression coping 300 and is therefore removed from the widened sulcus 110 as the custom impression coping 300 is withdrawn.

Figure 11:
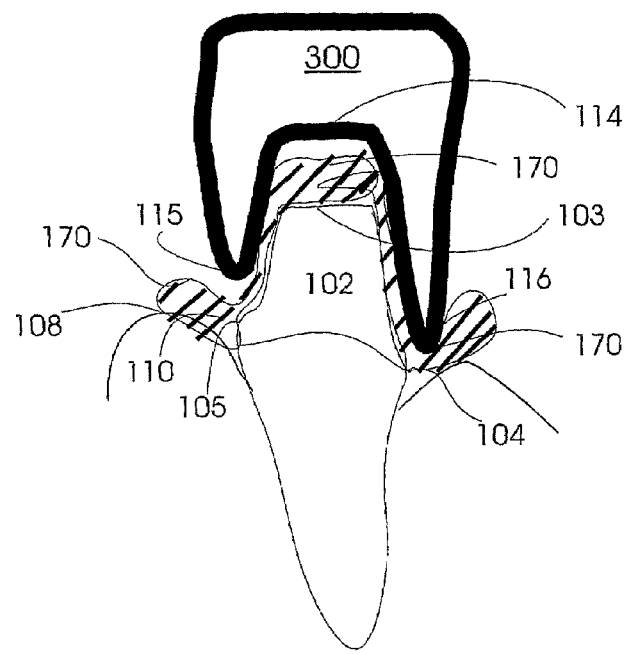
FIG. 11 is a longitudinal cross-sectional view similar to FIG. 4 illustrating the compression and flow of the retraction/ impression material as it extrudes precisely to adapt to the uneven and more apically located gingival margin of the custom impression coping.

FIG. 11 illustrates the custom impression coping 300 as it is compressed onto the tooth abutment 102. It should be noted that it is preferable that the custom impression coping 300 be centered over the tooth abutment 102 so that the retraction-impression paste be evenly distribute. The custom impression coping 300 has three functions. Firstly, it serves as a vehicle to transport the retraction impression material 170 to the abutment tooth 102; secondly it serves as a template which compresses the retraction impression material axially and gingivally precisely apical to the abutment margin; thirdly it serves as a vehicle to easily and quickly and atraumatically withdraw the retraction impression material from the sulcus.

Figure 12:
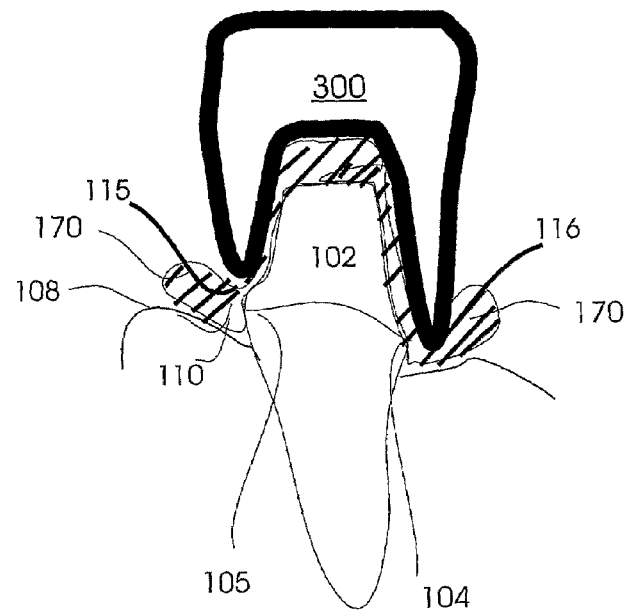
FIG. 12 is a longitudinal cross-sectional view similar to FIG. 9; demonstrating how the margins of the provisional restoration precisely guide the extrusion of retraction/impression material into the sulcus thereby producing precise and even confluent and atraumatic retraction and impression and demonstrating the extrusion of the excess material out of the sulcus.

FIG. 12 illustrates the custom impression coping 300 which is fully seated onto the prepared tooth abutment 102 demonstrating how the retraction-impression material retracts the gingiva 110 in an apical and lateral direction leaving the sulcus 108 open so that coincidentally an impression can be registered by the same retraction/impression material of the abutment margin 104 and 105 and the area below said margin.

Figure 13:
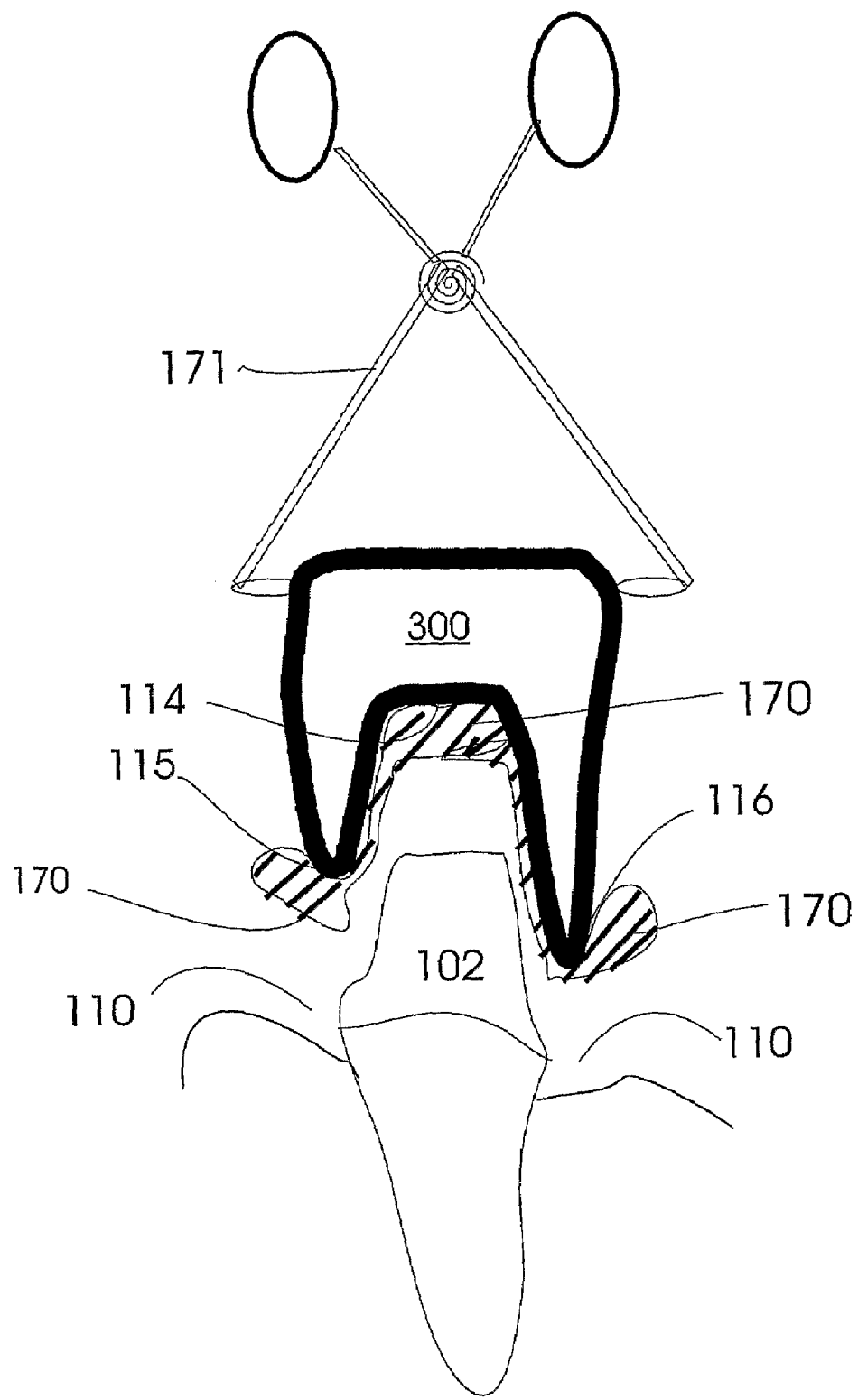
FIG. 13 is a longitudinal cross-sectional view illustrating the atraumatic removal of the retraction/impression material as it is attached to and coincidentally withdrawn with the custom impression coping by dental forceps.

FIG. 13 illustrates the atraumatic removal of the custom impression abutment 300 by dental forceps 171 with the associated low viscosity retraction impression material (170) which has been set and associated with the custom impression coping 300.

Figure 14:
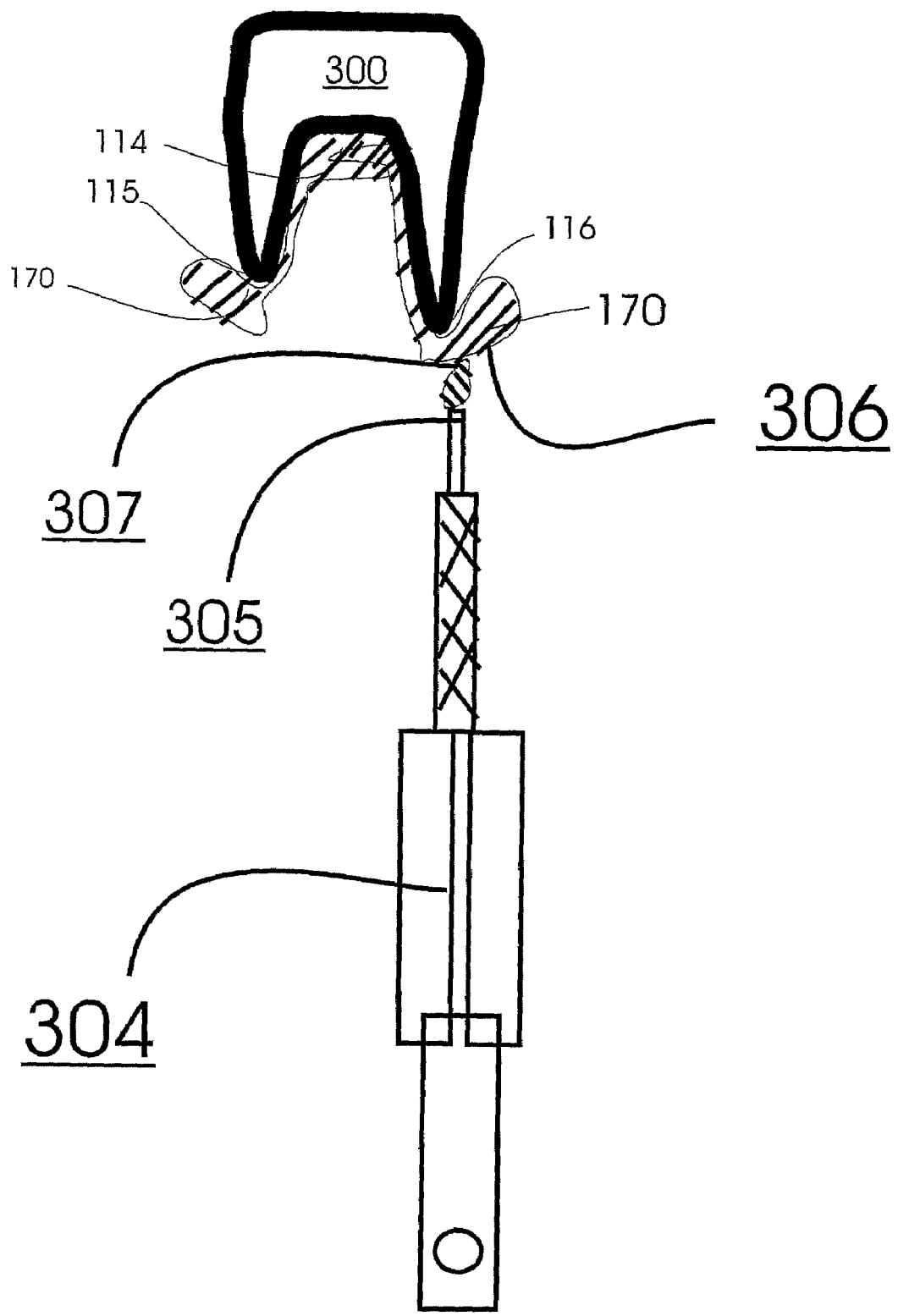
FIG. 14 is a longitudinal cross-sectional view illustrating the application of a light bodied reline material being applied to the outer perimeter of a retraction/impression material which is set and contained in a custom impression coping.

FIG. 14 illustrates the application of an embodiment of the present invention comprising a low viscosity "correction wash" retraction impression material onto the preferably lateral aspect of a margin of the set retraction impression material so that when the custom impression abutment 300 is replaced back into the sulcus, the margin of the impression may be repaired or refined. This may be affected by a dispensing gun 304 with preferably an ultra free tip 305 as very little retraction impression is required, or desired.

Figure 15:
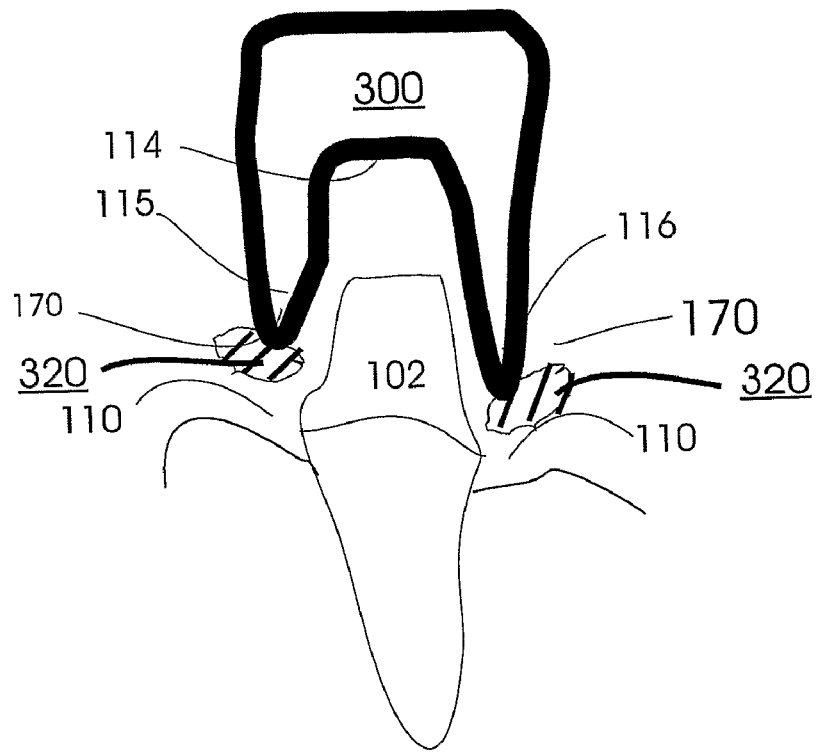
FIG. 15 is a longitudinal cross-sectional view illustrating the customized impression coping as referred to in FIG. 14 with unset reline material being placed and compressed over the prepared tooth abutment.

FIG. 15 illustrates the replacement of the custom impression abutment 300, associated with the unset low viscosity retraction impression material (320), onto the tooth abutment 102, and said unset retraction impression material is being compressed and directed into the sulcus.

Figure 16:
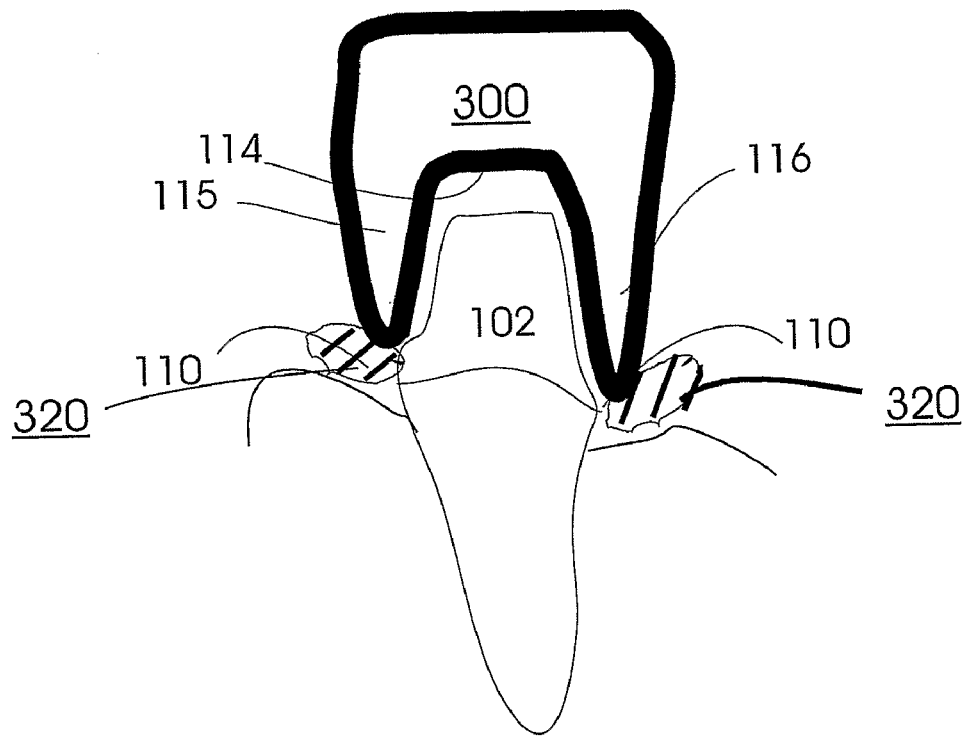
FIG. 16 is a longitudinal cross-sectional view illustrating the customized impression coping as referred to in FIG. 15 being further compressed over the prepared tooth abutment expressing and displacing fluids and debris out of the sulcus and displacing the gingival tissues in an apical and lateral direction and simultaneously capturing an accurate impression of the tooth abutment as well as the root surface apical to the prepared margin.

FIG. 16 illustrates the unset low viscosity retraction impression which is being compressed apically into the sulcus and which is being directed proximally towards the interior edge of the custom impression abutment 300 by the proximal slope of the gingival sulcus 110 so that an easy, simple, fast, accurate, predictable, simultaneous gingival retraction and complete abutment impression can be accomplished.

Figure 17:
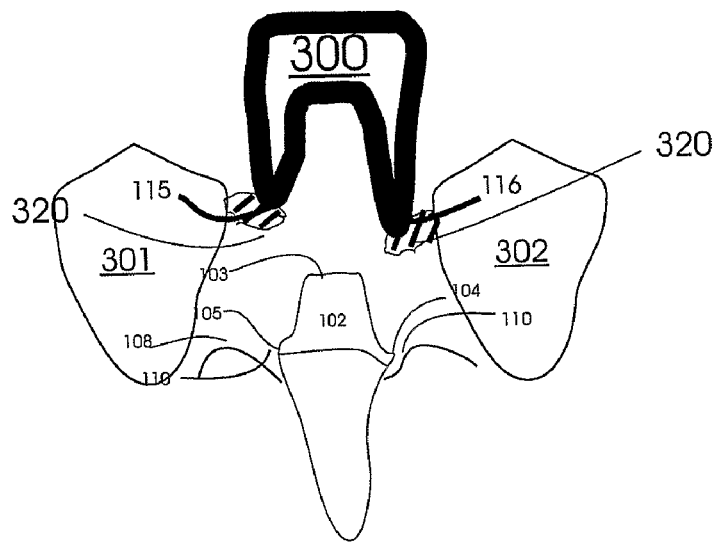
FIG. 17 is a longitudinal cross-sectional view similar to FIG. 15, illustrating teeth adjacent to the prepared tooth abutment.

FIG. 17. is similar to FIG. 15 but illustrates with adjacent teeth 301+302. It is preferable that the interproximal heights of contour of the custom impression coping 300 be reduced next to adjacent teeth 301 and 302.

Figure 18:
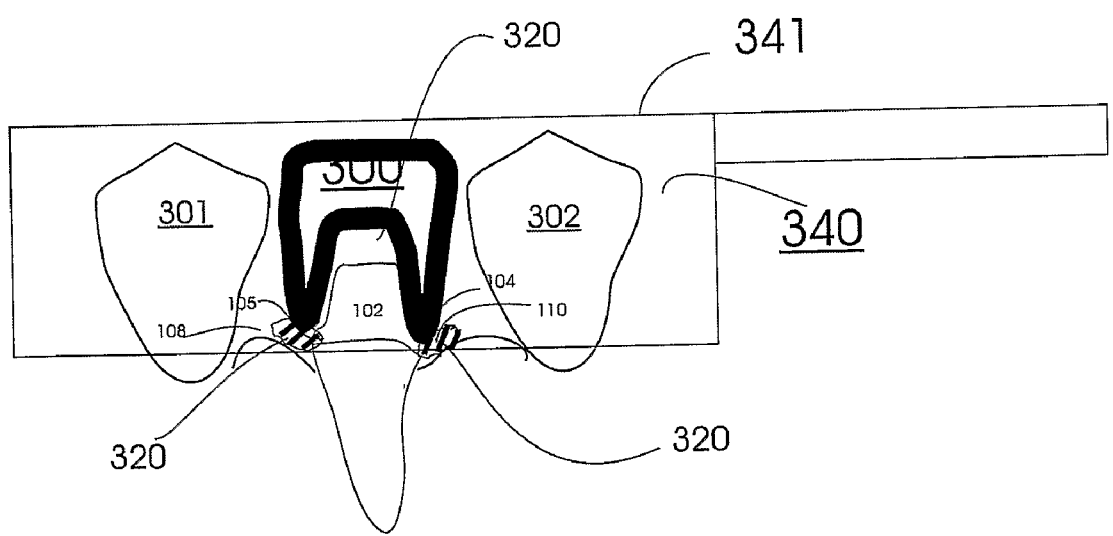
FIG. 18 is a longitudinal cross-sectional view similar to FIG. 16, illustrating teeth adjacent to the prepared tooth abutment and said custom impression coping containing set retraction/impression material which has been relined with light bodied retraction/impression material as well as the adjacent teeth has been covered by an impression tray containing conventional impression material.

FIG. 18. is similar to FIG. 16 but illustrates adjacent teeth 301+302 all of which are covered with an impression tray 341 containing impression material 340.

Figure 19:
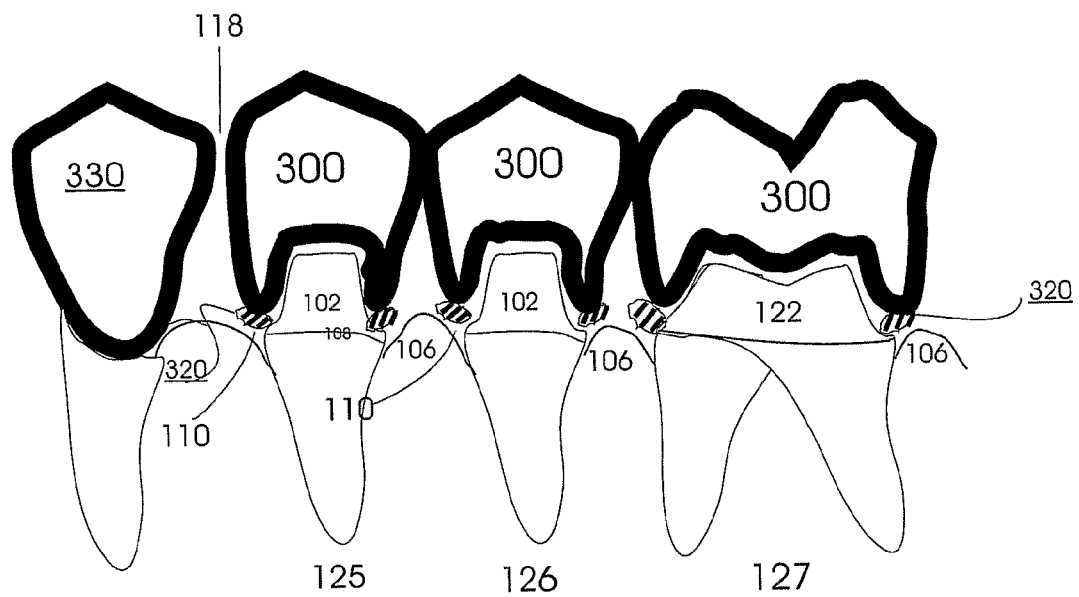
FIG. 19 is a longitudinal cross sectional view similar to FIG. 9 with a light bodied retraction/impression material which has been associated with the set heavier bodied retraction impression material which constitutes the custom impression coping.

FIG. 19. is similar to FIG. 16 but illustrates a plurality of abutments 125, 126, 127 and the proximal space 118 which has been created by removing the height of contour or super bulge of the proximal aspect of the custom impression coping preferably with a scalpel blade or bur or polishing wheel. The retraction/impression material 320 may be associated with the custom impression coping first and then carried with said custom impression coping into the sulcus or alternately, the retraction-impression material may firstly be placed into the sulcus, preferably with an auto mixing gun or syringe and then be covered with the custom impression coping.

Figure 20:
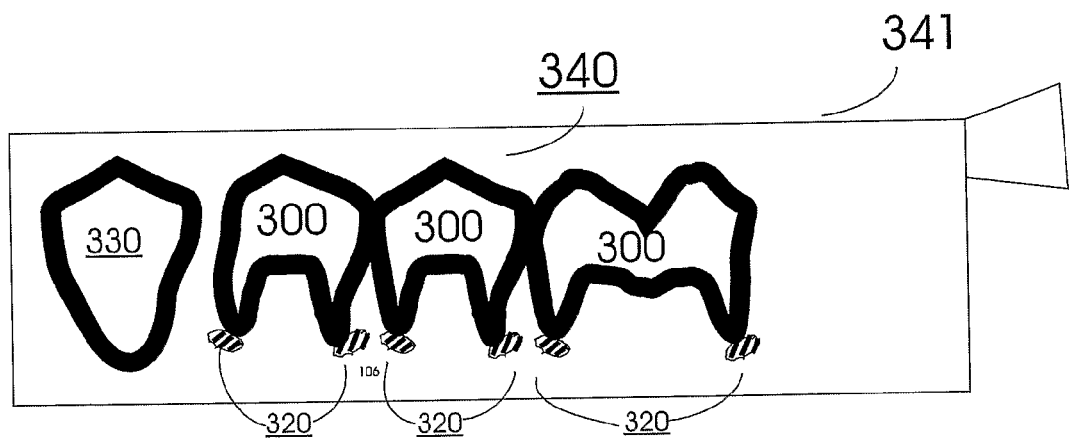
FIG. 20 is a longitudinal cross sectional view similar to FIG. 10 with a hardened or set light bodied retraction/impression material which has been associated with the set heavier bodied retraction impression material comprising the custom impression coping, the entirety which is contained in the set impression material of the over impression tray.

FIG. 20 illustrates the atraumatic removal of the plurality of custom impression abutments 300 which are embedded in the set impression material 340 contained in the impression tray 341

The above description of preferred embodiments should not be interpreted in a limiting manner since other variations, modifications, and refinements are also possible with the spirit and scope of the present invention. The scope of the invention is defined in the appended claims and their equivalents.

The invention claimed is:

1. A method of preparing a tooth for a dental procedure comprising:
   (A) removing a portion of the tooth to create a tooth abutment;
   (B) providing a dental device having a first retraction/impression material;
   (C) placing the dental device containing the first retraction/impression material onto the tooth abutment;
   (D) exerting pressure on the device to force at least some of the first retraction/impression material into a sulcus associated with the tooth, retracting the sulcus;
   (E) allowing the first retraction/impression material to set;
   (F) removing the dental device containing the set first retraction/impression material from the tooth abutment, the set first retraction/impression material defining a custom impression coping;
   (G) separating the custom impression coping from the dental device;
   (H) relining the custom impression coping with a second retraction/impression material or placing a second retraction/impression material in at least a portion of the sulcus associated with the tooth;
   (I) placing the custom impression coping onto the tooth abutment;
   (J) exerting pressure on the custom impression coping;
   (K) creating an over-impression over the custom impression coping;
   (L) removing the over-impression and the custom impression coping from the tooth abutment.

2. The method of preparing a tooth for a dental procedure as recited in claim 1, wherein the dental device is a preliminary impression having an interior cavity, and providing a dental device having a first retraction/impression material includes placing the first retraction/impression material into the interior cavity of the preliminary impression.

3. The method of preparing a tooth for a dental procedure as recited in claim 2, further comprising, before placing the first retraction/impression material into the interior cavity of the preliminary impression, lubricating the interior cavity of the preliminary impression.

4. The method of preparing a tooth for a dental procedure as recited in claim 1, further comprising removing the set first retraction/impression material from the custom impression coping.

5. The method of preparing a tooth for a dental procedure as recited in claim 4, wherein the set first retraction/impression material is removed from at least one of a proximal contact area, a distal contact area, and an occlusal area of the custom impression coping.

6. The method of preparing a tooth for a dental procedure as recited in claim 5, wherein the set first retraction/impression material is removed from the proximal contact area, the distal contact area, and the occlusal area of the custom impression coping.

7. The method of preparing a tooth for dental procedure as recited in claim 1, wherein relining the custom impression coping with a second retraction/impression material or placing a second retraction/impression material in at least a portion of the sulcus associated with the tooth is relining the custom impression coping with a second retraction/impression material.

8. The method of preparing a tooth for a dental procedure as recited in claim 7, wherein it is an interior cavity of the custom impression coping that is relined.

9. The method of preparing a tooth for a dental procedure as recited in claim 7, wherein it is an outside edge of the custom impression coping that is relined.

10. The method of preparing a tooth for dental procedure as recited in claim 1, wherein relining the custom impression coping with a second retraction/impression material or placing a second retraction/impression material in at least a portion of the sulcus associated with the tooth is placing a second retraction/impression material in at least a portion of the sulcus associated with the tooth.

11. The method of preparing a tooth for a dental procedure as recited in claim 10, wherein the second retraction/impression material is placed in an entirety of the sulcus associated with the tooth.

12. The method of preparing a tooth for a dental procedure as recited in claim 7, wherein the second retraction/impression material has a hardness that is less than a hardness of the first retraction/impression material.

13. The method of preparing a tooth for a dental procedure as recited in claim 12, wherein the hardness (durometer) of the first material is between 60 c.a. and 120 c.a. inclusive and the hardness (durometer) of the second material is less than 50 c.a.

14. The method of preparing a tooth for a dental procedure as recited in claim 7, wherein the second retraction/impression material has a viscosity that is less than a viscosity of the first retraction/impression material.

15. The method of preparing a tooth for a dental procedure as recited in claim 7, wherein creating an over-impression over the custom impression coping occurs while the second material is setting.

16. The method of preparing a tooth for a dental procedure as recited in claim 7, further comprising, before creating an over-impression over the custom impression, allowing the second material to set.

17. The method of preparing a tooth for a dental procedure as recited in claim 16, further comprising, after allowing the second material is allowed to set and before creating an over impression over the custom impression, relining the custom impression coping with a third retraction/impression material.

18. The method of preparing a tooth for a dental procedure as recited in claim 17, wherein it is an interior cavity of the custom impression coping that is relined with the third retraction/impression material.

19. The method of preparing a tooth for a dental procedure as recited in claim 17, wherein it is an outside edge of the custom impression coping that is relined with the third retraction/impression material.

20. The method of preparing a tooth for a dental procedure as recited in claim 16, further comprising, after allowing the second material is allowed to set and before creating an over-impression over the custom impression, relining the custom impression coping with a third retraction/impression material, placing a third retraction/impression material in at least a portion of the sulcus associated with the tooth.

21. The method of preparing a tooth for a dental procedure as recited in claim 20, wherein the third retraction/impression material is placed in an entirety of the sulcus associated with the tooth.

22. The method of preparing a tooth for a dental procedure as recited in claim 17, wherein the third retraction/impression material has a hardness that is less than a hardness of the first retraction/impression material.

23. The method of preparing a tooth for a dental procedure as recited in claim 22, wherein the hardness (durometer) of the first material is between 60 c.a. and 120 c.a. inclusive and the hardness (durometer) of the second material is less than 50 c.a.

24. The method of preparing a tooth for a dental procedure as recited in claim 17, wherein the third retraction/impression material has a viscosity that is less than a viscosity of the first retraction/impression material.

25. The method of preparing a tooth for a dental procedure as recited in claim 2, wherein the preliminary impression is used to create the over-impression over the custom impression coping.

26. The method of preparing a tooth for a dental procedure as recited in claim 1, wherein the dental device is selected from the group consisting of a stock tray, a custom tray, a triple tray, a cylinder, a template, a cap, and a tube.

27. The method of preparing a tooth for a dental procedure as recited in claim 1, wherein at least one item selected from the group consisting of a stock tray, a custom tray, a triple tray, a cylinder, a template, a cap, and a tube, is used to create the over-impression over the custom impression coping.

28. A method of preparing teeth for a dental procedure comprising carrying out the method of preparing a tooth for a dental procedure as recited in claim 1 on a plurality of teeth.

* * * * *